United States Patent
Jiao et al.

(10) Patent No.: US 8,927,523 B2
(45) Date of Patent: *Jan. 6, 2015

(54) COMPOUND SEA CUCUMBER PREPARATION AND MANUFACTURING METHOD THEREOF

(75) Inventors: Jian Jiao, Dalian (CN); Junjie Shao, Dalian (CN)

(73) Assignee: Dalian Haiyantang Biology Co., Ltd., Dalian, Liaoning (CN)

( * ) Notice: Subject to any disclaimer, the term of this patent is extended or adjusted under 35 U.S.C. 154(b) by 0 days.

This patent is subject to a terminal disclaimer.

(21) Appl. No.: 13/576,961

(22) PCT Filed: Mar. 3, 2011

(86) PCT No.: PCT/CN2011/071475
§ 371 (c)(1),
(2), (4) Date: Aug. 3, 2012

(87) PCT Pub. No.: WO2012/079310
PCT Pub. Date: Jun. 21, 2012

(65) Prior Publication Data
US 2012/0309710 A1    Dec. 6, 2012

(30) Foreign Application Priority Data
Dec. 14, 2010  (CN) .......................... 2010 1 0586833

(51) Int. Cl.
*A01N 43/04*    (2006.01)
*A61K 35/56*    (2006.01)
*A61K 36/258*   (2006.01)

(52) U.S. Cl.
CPC ............. *A61K 35/616* (2013.01); *A61K 36/258* (2013.01); *A61K 2236/39* (2013.01)
USPC .......................................................... 514/54

(58) Field of Classification Search
None
See application file for complete search history.

(56) References Cited

FOREIGN PATENT DOCUMENTS

| CN | 1858067 A | | 11/2006 |
| CN | 101143155 A | | 3/2008 |
| CN | 101416672 | * | 4/2009 |
| CN | 101416672 A | | 4/2009 |
| CN | 101451157 A | | 6/2009 |
| CN | 101700265 | * | 5/2010 |
| CN | 100998427 | * | 9/2010 |
| WO | 2007/005349 A2 | | 1/2007 |

* cited by examiner

*Primary Examiner* — Snigdha Maewall
(74) *Attorney, Agent, or Firm* — Novick, Kim & Lee, PLLC; Allen Xue

(57) ABSTRACT

A sea cucumber preparation and manufacturing method thereof, comprising steps as follows: put the cut and well-cleaned fresh sea cucumber or soaked sea cucumber into an airtight container; at 70~130° C., gelatinate for 1 min~20 h, freeze-dry till the water content is less than 10 wt %, then sequentially carry out coarse, ultra-micro and nanometer crushing till the fineness reaches 10~1000 nm. Add water into the sea cucumber nanometer powder to carry out proteinase enzymolysis, after the enzymolysis is finished, inactivate the proteinase, separate and take the supernatant and dry to get nanometer sea cucumber extract. Evenly mix the extract with panax pseudo-ginseng saponins extract at the proportion of 99~70%:1~30%. The content of the sea cucumber polysaccharide in the mixture is 2.5~8.0 wt %, the content of panax pseudo-ginseng saponins is 0.3~21.0 wt %. The compound preparation has complementary and synergistic effects on pharmacological effect. The side effects of single preparation can be eliminated through the compound preparation, the pharmacological functions of the sea cucumber or panax pseudo-ginseng single preparation are greatly enhanced, and can be used for anti-coagulation, diabetes and other various medicinal purposes.

20 Claims, No Drawings

COMPOUND SEA CUCUMBER PREPARATION AND MANUFACTURING METHOD THEREOF

TECHNICAL FIELD

The invention belongs to medicinal preparation of extract from mollusca and plant, relating to proteinase application and extract technology for polysaccharide, as well as preparation for dosage form of preparation.

BACKGROUND TECHNOLOGY

Sea cucumber is one of the eight sea food treasures in China, and its nourishing values are known to all. Wherein the sea cucumber polysaccharide is the most important active ingredient of sea cucumber and has a variety of physiological activities, according to the experiment and research, sea cucumber polysaccharides has remarkable effect against cardiovascular diseases. To develop directly after nanorizing the sea cucumber not only can sufficiently use the active ingredients such as sea cucumber polysaccharide, meanwhile, also can commonly sufficiently use the sea cucumber protein, lipid and so on.

Pseudo-ginseng is a specialty in southern Yunnan Province and is a panax plant, the meat quality of rootstock is like ginger shape, using for curing traumatic injuries, blood activation and stasis remove etc in folk. The main functional component of pseudo-ginseng is panax Pseudo-ginseng saponins widely used in medicinal healthcare field, and pharmaceutical enterprises develop many famous medicines such as Yunnan Baiyao, Blood-block Unlock series, Compound Salvia Miltiorrhiza Dripping Pills, Pien Tze Huang by using the special effect of pseudo-ginseng. Wherein, medicines made from panax Pseudo-ginseng saponins are generally called "Thrombus Unlock", at present blood-block unlock injections, blood-block unlock pills, blood-block capsules and blood-block unlock granules etc can be fund in the market. Blood-block unlock is the necessary Chinese patent drug of emergency department in all national hospitals, and also is mainly used in aspect to heart cerebrovascular diseases.

Modern science and technology development has confirmed the effect of the active ingredients in sea cucumber and pseudo-ginseng to human body, and numerous medicines and health care products are produced and appear in the market. However the important research subject at present is that whether compound preparation of each characteristic of sea cucumber and pseudo-ginseng etc has a better effect to human body health or not.

Sea cucumber compound preparation is mainly empty in the market at present, only a few such as Patent 200710114414.7 Compound Sea Cucumber Glycopeptide Oral Liquid, which is a compound sea cucumber oral liquid developed by using sea cucumber, matched with royal jelly and Chinese medicine extract, and the aiming crowd is unclear and the effect is unclear.

SUMMARY OF THE INVENTION

The purpose of the invention is to develop a product which has a better treatment and health care effect than only using sea cucumber or pseudo-ginseng through using the polysaccharide extracted from the atomized sea cucumber nanometer powder and directly matching with pseudo-ginseng or panax pseudo-ginseng saponins extract.

The technical proposal of the invention is to firstly gelatinate the sea cucumber, the gelatinated sea cucumber is crushed into nanometer particles sequentially by coarse crushing, ultra-micro crushing and nanometer crushing after freeze-drying, then prepare the extract by enzymolysis and separating the nanometer sea cucumber particles (active ingredient: sea cucumber polysaccharide), at last compound prepare the product with the sea cucumber extract and panax pseudo-ginseng saponins.

The detail operation steps of the proposal comprising:

(1) Raw material process: put the cut and well-cleaned fresh sea cucumber or soaked sea cucumber into an airtight container; cut the fresh sea cucumber and take out the viscus, wash them respectively and sufficiently, may use only sea cucumber body, also may grind with the sea cucumber viscus and put into an airtight container. The varieties of said fresh sea cucumber or soaked sea cucumber are common eatable sea cucumber such as sea stichopus or cucumaria frondosa; said soaked sea cucumber is made by soaking or desalinating dry sea cucumber, half-dried sea cucumber or saline sea cucumber.

(2) Heat and gelatination: heat at 70~130° C. for 1 min~20 h, preferably 100~105° C., 1 h.

(3) Freeze-dry: freeze-dry the gelatinated sea cucumber till the water content is less than 10 wt %. In order to be good for subsequent crushing process, a lower water content after drying is preferred, preferably water content less than 3%.

(4) Coarse crush: crush the freeze-dried sea cucumber. A higher power of equipment for coarse crushing is preferred, the crush time is short and generally sea cucumber powder with fineness of 10~300 mesh can be made within 1~20 min.

(5) Ultra-micro crush: ultra-micro crush the coarse crushed sea cucumber powder with an airflow crusher, to get the ultra-micro sea cucumber powder with fineness of 100~3000 mesh;

(6) Nanometer crush: nanometer crush the ultra-micro sea cucumber powder by the airflow crusher with a high energy ball grinding mill, the crush time is 4~20 h, preferably 10~12 h, the fineness can be up to 10~1000 nm. Wherein X-ray is used to detect the particle size distribution, in 0~300 nm range, the average particle size is 100~200 nm.

(7) Enzymolysis and separation: dissolve the nanometer sea cucumber powder with water at the mass ratio of 1:3~10, add proteinase at the ratio of nanometer sea cucumber powder:proteinase equal to 1 g:1010 mg and enzymolysis at corresponding pH value for 1~5 h at 40~70° C., then heat and inactivate the proteinase, centrifuge at high speed at 0~10° C., take the supernatant; the proteinase for enzymolysis can be various proteinases, such as bromelain, papain, alkali proteinase, neutral proteinase, flavourzyme, trypsase, meanwhile can be single proteinase for enzymolysis, and also can select two or more above mentioned proteinases for enzymolysis. Preferably mix the nanometer sea cucumber powder with water at the mass ratio of 1:7 evenly, use alkali proteinase acalase and trypsase to carry out double enzymolysis: the temperature for enzymolysis is 40~70° C., firstly adjust the pH value to 7~8, add alkali proteinase acalase according to the mass ratio between nanometer sea cucumber powder and proteinase equal to 1 g:0.1~10 mg, after enzymolysis for 0.1 h~5 h, adjust pH value to 8~10, add trypsase according to the mass ratio between nanometer sea cucumber powder and proteinase equal to 1 g:10 mg~1000 mg to enzymolysis for 0.1~5 h for the second time at 40~70° C. After the enzymolysis reaction is finished, heat the enzymolysis reaction solution at 90~100° C. for 1~20 min to inactivate the proteinase. Then filter, centrifuge and separate the enzymolysis product, take the enzymolysis supernatant and dry to get nanometer sea cucumber powder extract.

(8) Mix the nanometer sea cucumber extract with the panax pseudo-ginseng saponins extract at the ratio of nanometer sea cucumber extract:panax pseudo-ginseng saponins extract equal to 99~70 wt %:1~30 wt %.

This product is a gray or light brown powder and the main active ingredient is sea cucumber polysaccharide and panax pseudo-ginseng saponins (calculated by R1+Rb1+Rg1 ingredient total contents), the content of sea cucumber polysaccharide is 2.5%~8.0% and the content of panax pseudo-ginseng saponins is 0.3%~21%.

Various dosage forms, such as capsules, pills and granules can be made after mixing.

The present research shows that sea cucumber polysaccharide not only has anti-coagulation function, also can mobilize the capability of stem cell from the bone marrow, while panax pseudo-ginseng saponins can promote the mobilized hepatic stem cells to transform or differentiate into new myocardial cells or brain cells, so as to replace the myocardium or brain necrosis caused by ischemia. The compound preparation of nanometer sea cucumber and panax pseudo-ginseng saponins have complementary and collaboration effect in pharmacological effects, the side effect that sea cucumber polysaccharide can promote the blood platelet aggregation can be eliminated through the compound preparation with panax pseudo-ginseng saponins. The method of extracting the atomized sea cucumber nanometer powder and directly matching with panax pseudo-ginseng extract can greatly enhance the pharmacological functions of single formular of sea cucumber or pseudo-ginseng, and can be widely used in various medicinal purposes such as anti-coagulation, diabetes and so on.

DETAILED DESCRIPTION OF EMBODIMENTS

I. Manufacture of Compound Sea Cucumber Preparation

Example 1

(1) Raw material processing: cut the fresh sea stichopus, take out the viscus, sufficiently clean the sea cucumber wall, and put it into an airtight container.

(2) Gelatination: heat the container at 70~80° C. for 20 hours.

(3) Vacuum freeze-dry: freeze-dry the gelatinated sea cucumber till the water content is 0.1%.

(4) Coarse crush: crush the freeze-dried sea cucumber to get sea cucumber powder with fineness of 10~300 mesh.

(5) Ultra-micro crush: ultra-micro crush the coarse crushed sea cucumber powder with an airflow crusher, to get ultra-micro sea cucumber powder with fineness of 100~3000 mesh.

(6) Nanometer crush: nanometer crush, with a high energy ball grinding mill, the ultra-micro sea cucumber powder obtained by the airflow crusher, the nanometer crush time being 4 hours.

(7) Enzymolysis: add the nanometer sea cucumber powder with water at (the weight) ratio of 1:3 and mix up evenly, add bromelain at the ratio of nanometer sea cucumber powder:bromelain equal to 1 g:10 mg and enzymolysis for 5 hours at 40° C. under pH 6~7; after the enzymolysis reaction is finished, heat the enzymolysis reaction solution for 20 min at 90° C. Centrifuge and separate the enzymolysis product, take the enzymolysis supernatant, dry directly to get nanometer sea cucumber extract.

(8) Mix the nanometer sea cucumber extract with the panax pseudo-ginseng saponins extract at the ratio of nanometer sea cucumber extract:panax pseudo-ginseng saponins extract equal to 99%:1%.

The product is a light brown powder, and the main active ingredients are sea cucumber polysaccharide and panax pseudo-ginseng saponins (calculated by R1+Rb1+Rg1 ingredient total contents), wherein the content of sea cucumber polysaccharide is 7.8% and the content of panax pseudo-ginseng saponins is 0.5%.

The example product is carried out with the efficacy experiment of influence on blood coagulation parameter TT, RT by treating by irrigating stomachs of mice. The results are shown in Table 1.

Put the product into a capsule, 0.3 g for each capsule.

Example 2

(1) Raw material processing: cut the fresh cucumaria frondosa, take out the viscus, sufficiently clean the sea cucumber wall and the viscus respectively, and put them together into an airtight container.

(2) Gelatination: heat the container at 80~90° C. for 15 hours.

(3) Vacuum freeze-dry: freeze-dry the gelatinated sea cucumber till the water content is 1%.

(4) Coarse crush: crush the freeze-dried sea cucumber to get sea cucumber powder with fineness of 10~300 mesh.

(5) Ultra-micro crush: ultra-micro crush the coarse crushed sea cucumber powder with an airflow crusher, to get ultra-micro sea cucumber powder with fineness of 100~3000 mesh.

(6) Nanometer crush: nanometer crush, with a high energy ball grinding mill, the ultra-micro sea cucumber powder obtained by the airflow crusher, the nanometer crush time being 8 hours.

(7) Enzymolysis: add the nanometer sea cucumber powder with water at (the weight) ratio of 1:4 and mix up evenly, add alkaline proteinase at the ratio of nanometer sea cucumber powder:alkaline proteinase equal to 1 g:0.5 mg and enzymolysis for 2 hours at 65° C. under pH 6~7; after the enzymolysis reaction is finished, heat the enzymolysis reaction solution for 15 min at 95° C. Centrifuge and separate the enzymolysis product, take the enzymolysis supernatant, dry directly to get nanometer sea cucumber extract.

(8) Mix the nanometer sea cucumber extract with the panax pseudo-ginseng saponins extract at the ratio of nanometer sea cucumber extract:panax pseudo-ginseng saponins extract equal to 90%:10%.

The product is a light brown powder, and the main active ingredients are sea cucumber polysaccharide and panax pseudo-ginseng saponins (calculated by R1+Rb1+Rg1 ingredient total contents), wherein the content of sea cucumber polysaccharide is 4.6% and the content of panax pseudo-ginseng saponins is 6.2%.

The influences on TT and RT value by pure sea cucumber nanometer powder and those by the example product after treating mice by different treating ways are shown in Table 2.

Make capsules after mixing, 0.3 g for each capsule.

Example 3

(1) Raw material processing: soak the dry see stichopus in water, when is softened cut the sea stichopus wall, sufficiently clean the sea cucumber wall, and put it into an airtight container.

(2) Gelatination: heat the container at 90~100° C. for 10 hours.

(3) Vacuum freeze-dry: freeze-dry the gelatinated sea cucumber till the water content is 3%.

(4) Coarse crush, (5) Ultra-micro crush, and (6) Nanometer crush are the same as those in Example 2.

(7) Enzymolysis: add the nanometer sea cucumber powder with water at (the weight) ratio of 1:5 and mix up evenly, add trypsase at the ratio of nanometer sea cucumber powder:trypsase equal to 1 g:10 mg and enzymolysis for 5 hours at 45° C. under pH 8~9; after the enzymolysis reaction is finished, heat the enzymolysis reaction solution for 10 min at 100° C. Centrifuge and separate the enzymolysis product, take the enzymolysis supernatant, dry directly to get nanometer sea cucumber extract.

(8) Mix the nanometer sea cucumber extract with the panax pseudo-ginseng saponins extract at the ratio of nanometer sea cucumber extract:panax pseudo-ginseng saponins extract equal to 80%:20%.

The product is a light brown powder, and the main active ingredients are sea cucumber polysaccharide and panax pseudo-ginseng saponins (calculated by R1+Rb1+Rg1 ingredient total contents), wherein the content of sea cucumber polysaccharide is 6.3% and the content of panax pseudo-ginseng saponins is 10.9%.

Experiment is carried out with respect to the influence on fasting plasma glucose effects of experimental diabetic mice caused by alloxan, and the results are shown in Table 3.

Make capsules with mixed powder, 0.3 g for each capsule.

Example 4

1) Raw material processing: cut the saline dry sea stichopus, desalt it in water, when the saline dry sea stichopus is softened cut the sea stichopus wall, sufficiently clean, and put it into an airtight container.

(2) Gelatination: heat the container at 100~105° C. for 5 hours.

(3) Vacuum freeze-dry: freeze-dry the gelatinated sea cucumber till the water content is 5%.

(4) Coarse crush and (5) Ultra-micro crush are the same as those described in example 2.

(6) Nanometer crush: nanometer crush, with a high energy ball grinding mill, the ultra-micro sea cucumber powder obtained by the airflow crusher, the nanometer crush time being 12 hours.

(7) Enzymolysis: add the nanometer sea cucumber powder with water at (the weight) ratio of 1:6 and mix up evenly, add neutral proteinase at the ratio of nanometer sea cucumber powder:neutral proteinase equal to 1 g:1 mg and enzymolysis for 1 hours at 50° C. under pH 6.7~7; after the enzymolysis reaction is finished, heat the enzymolysis reaction solution for 5 min at 100° C. Centrifuge and separate the enzymolysis product, take the enzymolysis supernatant, dry directly to get nanometer sea cucumber extract.

(8) Mix the nanometer sea cucumber extract with the panax pseudo-ginseng saponins extract at the ratio of nanometer sea cucumber extract:panax pseudo-ginseng saponins extract equal to 70%:30%.

The product is a light brown powder, and the main active ingredients are sea cucumber polysaccharide and panax pseudo-ginseng saponins (calculated by R1+Rb1+Rg1 ingredient total contents), wherein the content of sea cucumber polysaccharide is 5.4% and the content of panax pseudo-ginseng saponins is 15.2%.

Make capsules with mixed powder, 0.3 g for each capsule.

Example 5

(1) Raw material processing: sork the saline dry sea stichopus, when it is softened heat the saline sea stichopus in water of 100~105° C. for 1 hour, cut the saline sea stichopus, sufficiently clean, desalt and at the same time sork the saline sea stichopus wall with pure water, and put the sea stichopus wall into an airtight container.

(2) Gelatination: heat the container at 105~110° C. for 2 hours.

(3) Vacuum freeze-dry: freeze-dry the gelatinated sea cucumber till the water content is 7%.

(4) Coarse crush and (5) Ultra-micro crush are the same as those described in example 1.

(6) Nanometer crush: nanometer crush, with a high energy ball grinding mill, the ultra-micro sea cucumber powder obtained by the airflow crusher, the nanometer crush time being 16 hours.

(7) Enzymolysis: add the nanometer sea cucumber powder with water at (the weight) ratio of 1:7 and mix up evenly, add alkaline proteinase at the ratio of nanometer sea cucumber powder:alkaline proteinase equal to 1 g:0.1 mg and enzymolysis for 3 hours at 65° C. under pH 7~8; and then adjust the temperature to 45° C., add trypsase at the ratio of nanometer sea cucumber powder:trypsase to 1 g:10 mg and enzymolysis for 3 hours under pH 8~9, after the enzymolysis reaction is finished, heat the enzymolysis reaction solution for 10 min at 100° C. Centrifuge and separate the enzymolysis product, take the enzymolysis supernatant, dry directly to get nanometer sea cucumber extract.

(8) Mix the nanometer sea cucumber extract with the panax pseudo-ginseng saponins extract at the ratio of nanometer sea cucumber extract:panax pseudo-ginseng saponins extract equal to 80%:20%.

The product is a light brown powder, and the main active ingredients are sea cucumber polysaccharide and panax pseudo-ginseng saponins (calculated by R1+Rb1+Rg1 ingredient total contents), wherein the content of sea cucumber polysaccharide is 4.4% and the content of panax pseudo-ginseng saponins is 7.9%.

After mixing make tablet at the ratio of raw material:excipients equal to 2:1

Example 6

(1) Raw material processing: soak the dry cucumaria frondosa, when it is softened cut the cucumaria frondosa wall, sufficiently clean, and put into an airtight container.

(2) Gelatination: heat the container at 110~120° C. for 1 hours.

(3) Vacuum freeze-dry: freeze-dry the gelatinated sea cucumber till the water content is 9%.

(4) Coarse crush and (5) Ultra-micro crush are the same as those described in example 1.

(6) Nanometer crush: nanometer crush, with a high energy ball grinding mill, the ultra-micro sea cucumber powder obtained by the airflow crusher, the nanometer crush time being 18 hours.

(7) Enzymolysis: add the nanometer sea cucumber powder with water at (the weight) ratio of 1:8 and mix up evenly, add alkaline proteinase at the ratio of nanometer sea cucumber powder:alkaline proteinase equal to 1 g:0.1 mg and enzymolysis for 1 hours at 65° C. under pH 7~8; and then add alkaline proteinase at the ratio of nanometer sea cucumber powder:alkaline proteinase to 1 g:0.1 mg and enzymolysis for 3 hours under pH 7~8 at 65° C., after the enzymolysis reaction is finished, heat the enzymolysis reaction solution for 10 min at 100° C. Centrifuge and separate the enzymolysis product, take the enzymolysis supernatant, dry directly to get nanometer sea cucumber extract.

(8) Mix the nanometer sea cucumber extract with the panax pseudo-ginseng saponins extract at the ratio of nanometer sea cucumber extract:panax pseudo-ginseng saponins extract equal to 90%:10%.

The product is a light brown powder, and the main active ingredients are sea cucumber polysaccharide and panax pseudo-ginseng saponins (calculated by R1+Rb1+Rg1 ingredient total contents), wherein the content of sea cucumber polysaccharide is 2.6 and the content of panax pseudo-ginseng saponins is 3.2%.

After mixing make granules at the ratio of raw material to excipients equal to 1:1.

Example 7

(1) Raw material processing: cut the fresh sea stichopus, take out the viscus, sufficiently clean the sea cucumber wall, and put it into an airtight container.

(2) Gelatination: heat the container at 120~130° C. for 10 minutes.

(3) Vacuum freeze-dry: freeze-dry the gelatinated sea cucumber till the water content is 10%.

(4) Coarse crush and (5) Ultra-micro crush are the same as those described in example 1.

(6) Nanometer crush: nanometer crush, with a high energy ball grinding mill, the ultra-micro sea cucumber powder obtained by the airflow crusher, the nanometer crush time being 20 hours.

(7) Enzymolysis: add the nanometer sea cucumber powder with water at (the weight) ratio of 1:10 and mix up evenly, add neutral proteinase at the ratio of nanometer sea cucumber powder:neutral proteinase equal to 1 g:0.8 mg and enzymolysis for 1 hours at 50° C. under pH 6.7~7, and add alkali proteinase at the ratio of nanometer sea cucumber powder:alkali proteinase equal to 1 g:1 mg and enzymolysis for 1 hours at 65° C. under pH 7~8, and then adjust the temperature to 45° C., add trypsase at the ratio of nanometer sea cucumber powder:trypsase equal to 1 g:10 mg and enzymolysis for 1 hours under pH 8~9, after the enzymolysis reaction is finished, heat the enzymolysis reaction solution for 10 min at 100° C. Centrifuge and separate the enzymolysis product, take the enzymolysis supernatant, dry directly to get nanometer sea cucumber extract.

(8) Mix the nanometer sea cucumber extract with the panax pseudo-ginseng saponins extract at the ratio of nanometer sea cucumber extract:panax pseudo-ginseng saponins extract equal to 95%:5%.

The product is a light brown powder, and the main active ingredients are sea cucumber polysaccharide and panax pseudo-ginseng saponins (calculated by R1+Rb1+Rg1 ingredient total contents), wherein the content of sea cucumber polysaccharide is 7.5% and the content of panax pseudo-ginseng saponins is 3.2%.

Make capsules with mixed powder, 0.3 g for each capsule.

Example 8

(1) Raw material processing: cut the fresh sea stichopus, take out the viscus, sufficiently clean the sea cucumber wall, and put it into an airtight container.

(2) Gelatination: heat the container at 105~110° C. for 40 minutes.

(3) Vacuum freeze-dry: freeze-dry the gelatinated sea cucumber till the water content is 9%.

(4) Coarse crush, (5) Ultra-micro crush and (6) Nanometer crush are the same as those described in example 7.

(7) Enzymolysis: add the nanometer sea cucumber powder with water at (the weight) ratio of 1:9 and mix up evenly, add alkali proteinase at the ratio of nanometer sea cucumber powder:alkali proteinase equal to 1 g:10 mg and enzymolysis for 1 hours at 65° C. under pH 7~8, and then adjust the temperature to 45° C., add trypsase at the ratio of nanometer sea cucumber powder:trypsase equal to 1 g:100 mg and enzymolysis for 1 hours under pH 8~9, after the enzymolysis reaction is finished, heat the enzymolysis reaction solution for 10 min at 100° C. Centrifuge and separate the enzymolysis product, take the enzymolysis supernatant, dry directly to get nanometer sea cucumber extract.

(8) Mix the nanometer sea cucumber extract with the panax pseudo-ginseng saponins extract at the ratio of nanometer sea cucumber extract:panax pseudo-ginseng saponins extract equal to 80%:20%.

The product is a light brown powder, and the main active ingredients are sea cucumber polysaccharide and panax pseudo-ginseng saponins (calculated by R1+Rb1+Rg1 ingredient total contents), wherein the content of sea cucumber polysaccharide is 3.3% and the content of panax pseudo-ginseng saponins is 6.8%.

After mixing make granules at the ratio of raw material to excipients equal to 1:1.

Example 9

(1) Raw material processing: cut the fresh sea cucumber, take out the viscus, sufficiently clean the sea cucumber wall, and put it into an airtight container.

(2) Gelatination: heat the container at 100~105° C. for 120 minutes.

(3) Vacuum freeze-dry: freeze-dry the gelatinated sea cucumber till the water content is 3%.

(4) Coarse crush, (5) Ultra-micro crush and (6) Nanometer crush are the same as those described in example 7.

(7) Enzymolysis: add the nanometer sea cucumber powder with water at (the weight) ratio of 1:6 and mix up evenly, add alkali proteinase at the ratio of nanometer sea cucumber powder:alkali proteinase equal to 1 g:5 mg and enzymolysis for 1 hours at 65° C. under pH 7~8, and then adjust the temperature to 45° C., add trypsase at the ratio of nanometer sea cucumber powder:trypsase equal to 1 g:1000 mg and enzymolysis for 1 hours under pH 8~9, after the enzymolysis reaction is finished, heat the enzymolysis reaction solution for 10 min at 100° C. Centrifuge and separate the enzymolysis product, take the enzymolysis supernatant, dry directly to get nanometer sea cucumber extract.

(8) Mix the nanometer sea cucumber extract with the panax pseudo-ginseng saponins extract at the ratio of nanometer sea cucumber extract:panax pseudo-ginseng saponins extract equal to 90%:10%.

After mixing make tablet at the ratio of raw material: excipients equal to 2:1

The product is a light brown powder, and the main active ingredients are sea cucumber polysaccharide and panax pseudo-ginseng saponins (calculated by R1+Rb1+Rg1 ingredient total contents), wherein the content of sea cucumber polysaccharide is 4.7% and the content of panax pseudo-ginseng saponins is 4.1%.

II. Laboratory Efficacy Experiment of Mixture of Nanometer Sea Cucumber Extract and Panax Pseudo-Ginseng Saponins Extract 1. Influence to Blood Coagulation Time Parameter TT, RT by Treating by Irrigating Stomachs of Mice: see Table 1

TABLE 1

Influence to TT and RT 3 days after treating with compound sea cucumber preparation by irrigating stomachs of mice (n = 10, x ± s)

| Group | Dosage | TT (s) | TT Extension % | RT (s) | RT Extension % |
|---|---|---|---|---|---|
| NS | — | 5.64 ± 0.62 | — | 12.8 ± 10.2 | — |
| compound sea cucumber preparation | 0.3 g/kg | 7.08 ± 0.64 *** | 25.5 | 67.0 ± 8.5 *** | 423.4 |
| compound sea cucumber preparation | 0.15 g/kg | 6.56 ± 0.53 *** | 16.3 | 50.3 ± 11.3 *** | 293.0 |

Note:
*** P < 0.001 compared with normal saline group

2. Influences to TT Value and RT Value of Pure Sea Cucumber Nanometer Powder and Compound Sea Cucumber Preparation after Treating Mice Through Different Treat Ways:

(1) mice: Kunming variety, male, weight 23~25 g.

(2) determination of thrombin time (TT): Add blood plasma to be determined 50 uL, 1 mol/L pH7.4 Tris-HCL buffer solution 50 uL and 5 u/ml thrombin solution 50 uL into the determination cup of the blood coagulation analyzer sequentially, and the blood coagulation analyzer records the blood coagulation time automatically while the thrombin solution is added. The time from that the thrombin solution is added to that the blood coagulation is formed is recorded as blood plasma coagulation time, called thrombin time for short.

(3) Determination of re-calcification time (RT): Add blood plasma to be determined 100 μL, then add 0.025 mol/L CaCl2 solution 100 μL into the determination cup of the blood coagulation analyzer sequentially, and the blood coagulation analyzer records the blood coagulation time (re-calcification time) automatically while the CaCl2 solution is added.

(4) Animal experiment (i) Treating by injection from caudal vein of the mice: Accurately weigh sea cucumber nanometer powder or compound sea cucumber preparation 100 mg, add distilled water 5 ml, mix by rotating at 2800 r/min for 30 seconds, then centrifuge at 3000 r/min for 15 min, take the supernatant that is sea cucumber nanometer powder or compound sea cucumber preparation aqueous extract for reservation.

45 Kunming variety mice are divided into 3 groups randomly, those are normal saline group, nanometer sea cucumber powder group and compound sea cucumber preparation group, 15 mice for each group. The normal saline group is injected with normal saline 0.1 ml/10 g weight from the caudal vein, while the sea cucumber nanometer powder group and the compound sea cucumber preparation group are respectively injected with above said sea cucumber aqueous extract 0.1 ml/10 g weight from the caudal vein. 15 min after the injection, collect blood 0.45 ml on the eyeballs of the mice, add 0.05 ml 3.8% sodium citrate anti-coagulation, then adding 0.2 ml normal saline, centrifuge for 10 min at 3000 r/min after being mixed evenly, take the supernatant to determine the TT and RT values.

(ii) Treating by injection from abdomen of the mice: 18 Kunming variety mice are divided into 3 groups randomly, those are normal saline group, nanometer sea cucumber powder group and compound sea cucumber preparation group, 6 mice for each group. The normal saline group is injected with normal saline 0.2 ml/10 g weight from the abdomen, while the sea cucumber nanometer powder group and the compound sea cucumber preparation group are respectively injected with 50 mg/ml common sea cucumber powder and nanometer powder suspension 0.2 ml/10 g weight from the abdomen. 30 min after the injection from the abdomen, collect blood 0.45 ml on the eyeballs of the mice, add 0.05 ml 3.8% sodium citrate anti-coagulation, then adding 0.2 ml normal saline, centrifuge for 10 min at 3000 r/min after being mixed evenly, take the supernatant to determine the TT and RT values.

(iii) Treating by irrigating stomachs of the mice: 60 Kunming variety mice are divided into 6 groups, those are respectively 2 groups for normal saline group, nanometer sea cucumber powder group and compound sea cucumber preparation group, which are respectively treated by irrigating stomachs for 1 week and 2 weeks, 10 mice for each group. The normal saline group is treated by irrigating stomachs with normal saline 0.2 ml/10 g weight, while the sea cucumber nanometer powder group and the compound sea cucumber preparation group are respectively treated by irrigating stomachs with 50 mg/ml sea cucumber nanometer powder and compound sea cucumber preparation suspension 0.2 ml/10 g weight, (1 g/kg weight), twice for one day. Collect blood 0.45 ml on the eyeballs of the mice 1 h after the last stomach irrigation, add 0.05 ml 3.8% sodium citrate anti-coagulation, then adding 0.2 ml normal saline, centrifuge for 10 min at 3000 r/min after being mixed evenly, take the supernatant to determine the TT and RT values.

(5) Results

As shown in Table 2, after the mice are treated by the caudal intravenous injection, the abdomen injection and 2 weeks stomach irrigation, compared with NS group, RT values of the sea cucumber nanometer groups are respectively extended for 1259.46%, 236.54% and 284.04%, compared with NS group, RT values of the compound sea cucumber preparation groups are respectively extended for 1895.95%, 698.08% and 717.02%, and all have statistical significances (P<0.01), and the RT extension of the compound sea cucumber preparation is more significant than RT extension of nanometer powder; compared with RT values of nanometer powder groups, RT values of compound sea cucumber preparation groups are respectively extended for 46.82%, 137.14% and 112.74%, and the differences between the two groups have statistical significances (P<0.01). Compared with NS group, although the TT values have extension trend after treating by injection and orally taking, but have no statistical significances (P>0.05). After the mice are treated by irrigating stomachs for 1 week, compared with NS group, RT values of sea cucumber nanometer powder group and compound sea cucumber preparation group are all extended significantly, respectively for 641.18% and 905.88%, and have statistical significances; although RT of the nanometer powder is extended for 35.71% compared with common powder group, the differences between the two groups have no statistical significances (P>0.05). The detail summary of the experiment see Table 2:

A-3. FPG Determination:

Determine the fasting plasma glucose (FPG) for mice of each group at 7th day, 14th day and 28th day with Germany Roche Superior IV type glucose meter, and record the weights of mice.

B. Influences of Compound Sea Cucumber Preparation to Glucose Tolerance of Experimental Diabetic Mice Caused by Alloxan:

Building of mice high glucose model, animal grouping and treating ways are the same as above description. After mice of each group are determined fasting plasma glucose (FPG) fasting for 5 h with Germany Roche Superior IV type glucose meter at 28th treating day, mice are treated with 2 g/kg glu-

TABLE 2

Influences to TT value and RT value after treating by different ways to mice

| Treating way | NS group TT | | Nanometer sea cucumber powder | | | | Compound sea cucumber preparation | | |
|---|---|---|---|---|---|---|---|---|---|
| | | RT | TT | RT | RT extension (%, compared with NS group) | TT | RT | RT extension (%, compared with NS group) | RT extension (%, compared with common powder group) |
| Intravenous injection | 18.4 ± 6.1 | 7.4 ± 1.8 | 23.8 ± 8.3 | 100.6** ± 19.6 | 1259.46 | 15.6 ± 2.4 | 147.7**Δ ± 32.0 | 1895.95 | 46.82 |
| abdomen injection | 15.7 ± 0.8 | 5.2 ± 1.5 | 24.7 ± 2.3 | 17.5** ± 3.1 | 236.54 | 25.5 ± 2.5 | 41.5**Δ ± 2.2 | 698.08 | 137.14 |
| Stomach irrigation for 1 week | 14.7 ± 7.0 | 5.1 ± 1.9 | 18.2 ± 7.4 | 37.8** ± 36.3 | 641.18 | 19.1 ± 7.6 | 51.3** ± 38.3 | 905.88 | 35.71 |
| Stomach irrigation for 2 weeks | 13.8 ± 6.2 | 9.4 ± 8.9 | 18.5 ± 5.0 | 36.1* ± 34.6 | 284.04 | 18.2 ± 3.6 | 76.8**Δ ± 42.1 | 717.02 | 112.74 |

*P < 0.05 compared with normal saline group;
**P < 0.01 compared with normal saline group;
ΔP < 0.01 compared with nanometer powder group 3. Influences of Compound Sea Cucumber Preparation to Fasting Blood-Glucose Caused by Alloxan of Mice A. Experiment Design:

A-1. High Plasma Glucose Model Building for Mice:

Take male, 18~22 g Kunming variety mice, randomly take 10 mice from them as normal control group. Other mice are injected with alloxan 50 mg/kg after fasting (water is allowed) for 16 h, determine the fasting plasma glucose (FPG) fasting for 5 h after the mice are stable for 15 days, mice with FPG>10 mmol/L are high plasma glucose model mice.

A-2. Animal Grouping and Treating:

10 mice for normal control group. Take 40 high plasma glucose mice, randomly divide into high plasma glucose model group, compound sea cucumber preparation high dosage (0.5 g/kg) group, compound sea cucumber preparation low dosage (0.25 g/kg) group and positive drug metformin 200 mg/kg group.

Mice of the compound sea cucumber preparation high dosage group and the compound sea cucumber preparation low dosage group are respectively treated with 0.025 g/ml and 0.0125 g/ml suspension of compound sea cucumber preparation and normal saline 0.2 mL/10 gBW by irrigating stomachs, mice of the metformin 200 mg/kg group are treated with 10 mg/ml metformin normal saline solution 0.2 mL/10 gBW by irrigating stomachs, while mice of the normal control group and high plasma glucose model group are treated with equal volume of normal saline by irrigating stomachs. Mice of each group are treated twice each day (b.i.d) continuously for 4 weeks.

cose by abdomen injection, to determine the glucose value 30 min, 60 min, 120 min and 240 min after glucose load, and calculate the area under the glucose tolerance curve (AUC) according to trapezoid area method as formula below:

$$AUC(\text{mmol}\cdot\text{h/L}) = \sum_{i=1}^{n-1} \frac{C_i + C_{i+1}}{2} \cdot \Delta t$$

wherein, C is the plasma glucose value (mmol/L), t is the time after glucose load (h), i is the glucose value number; C0, C1, C2, C3, C4 are respectively plasma glucose value of before glucose load (0 min) and 30 min, 60 min, 120 min and 240 min after glucose load.

C. Effects of Compound Sea Cucumber Preparation to Insulin Resistance HepG2 Cell Model:

C-1. Cell Line:

Human liver cancer cell line HepG2 provided by Dalian Medical University is vaccinated in a DMEM culture medium which contains 10% volume fraction of fetal calf serum (supplementing penicillin, streptomycin 100 $U\cdot L^{-1}$ respectively), and the culture medium is placed in a 5% CO2 cell culture box at 37° C. HepG2 cells grow anchorage-dependently, digesting the cells by 0.25% pancreatic enzymes, the cells passage 1 time every 3 days, then taking cells in logarithmic phase for experiment.

C-2. Solution Preparation:

Preparation for sea cucumber N powder solution: dissolve with DMEM culture solution, then prepare mother solution with concentration of 1600 mg/L, then dilute the mother solution at equal ratio to required concentration according to specific situation.

Preparation for metformin solution: dissolve with DMEM culture solution, the concentration is 30 mg/L.

C-3. Building Insulin Resistance HepG2 Cell Model:

Digest monolayer culture HepG2 cells with 0.25% pancreatin, prepare single cell suspension with DMEM culture solution containing 10% fetal calf serum, adjust the cell concentration to $5 \times 10^4 \cdot ml^{-1}$ and total amount 200 uL for each well to vaccinate on 96-well cell culture plate. Incubate for 8 h in culture box in the conditions of 37° C. and 5% CO2 to form monolayer anchorage-dependent cells. Wash the cells twice with DMEM culture solution without fetal calf serum, then incubate the cells for 16 h with $5 \times 10^{-7}$ mol·$L^{-1}$ insulin culture solution in culture box in the conditions of 37° C. and 5% CO2. The HepG2 cells incubated for 16 h with insulin culture solution are model cells.

C-4 Grouping, Treating and Index Determination:

Count the prepared cell suspension, adjust the cell concentration to $5 \times 10^4 \cdot ml^{-1}$, vaccinate on 96-well cell culture plate, 8-well in duplicate for each group, total amount of 200 uL for each well. The experiment is divided into 5 groups: normal control group, insulin resistance model group, compound sea cucumber preparation high and low dosage groups and metformin positive control group. Except the normal control group, each other group is incubated for 16 h after adding insulin with ultimate concentration of $5 \times 10^{-7}$ mol·$L^{-1}$ into culture solution so as to form insulin resistance model. After model formation, cells are incubated with culture solution without insulin, each treating group is respectively incubated with culture solutions at ultimate concentrations of compound sea cucumber preparation 2.5 g·$L^{-1}$, compound sea cucumber preparation 5.0 g·$L^{-1}$ and metformin 30 mg·$L^{-1}$·24 h after treating, detect the glucose in the culture solution with glucose oxidase method, minus the glucose average value of blank duplicate wells of unvaccinated cells to calculate the glucose consumptions of each porocyte. Determinate the content of glycerin in the culture solution with GPO-POD enzyme method, minus the average glycerin content of blank duplicate wells of unvaccinated cells to calculate the glycerin consumption of each porocyte.

C-5. Determination the Influence of Drug to Cell Proliferation with MTT Method

Prepare MTT culture solution with 5 g·$L^{-1}$ MTT basic solution and serum free DMEM culture solution according to volume ratio of 1:9, after the cell glucose consumption experiment and glycerin consumption experiment are finished and the culture solution to be determined is taken out, add MTT culture solution to each well, culture continuously at 37° C., terminate the culture after 4 h, and carefully draw and abandon the culture supernatant in the well, add 200 μL dimethyl sulfoxide for each well, vibrate 10 min to dissolve the crystals sufficiently, determine the absorbency value of each well in a micro-plate reader, calculate the cell survival proportion to evaluate the influences of drug to cell proliferation.

D. Results:

D-1 Influences of Compound Sea Cucumber Preparation to Fasting Plasma Glucose of Experimental Diabetic Mice Caused by Alloxan

TABLE 3

Influences of compound sea cucumber preparation to fasting plasma glucose of experimental diabetic mice caused by alloxan (n = 10, x ± s)

| Group | Fasting Plasma Glucose (FPG, mmol/L) | | | | | | | | Weight 28 days after treating(g) |
|---|---|---|---|---|---|---|---|---|---|
| | 7 days after treating | | 14 days after treating | | 21 days after treating | | 28 days after treating | | |
| | FPG | Reduce % | FPG | Reduce % | FPG | Reduce % | FPG | Reduce % | |
| Blank control group | 7.18 ± 0.74 | — | 6.91 ± 0.83 | — | 7.19 ± 0.58 | — | 7.35 ± 0.62 | — | 38.12 ± 1.70 |
| High plasma glucose model group | 24.01 ± 3.02Δ | — | 29.65 ± 2.07Δ | — | 30.05 ± 2.07Δ | — | 30.16 ± 2.40Δ | — | 25.64 ± 4.10Δ |
| Metformin 200 mg/kg | 18.80 ± 2.77** | 21.7% | 24.59 ± 4.17** | 17.1% | 21.18 ± 3.12** | 29.5% | 20.72 ± 3.03** | 31.3% | 31.76 ± 1.74** |
| Compound sea cucumber preparation 0.5 g/kg | 21.54 ± 3.58 | 10.3% | 26.79 ± 2.21 | 9.6% | 23.62 ± 2.86** | 21.4% | 21.54 ± 3.43** | 28.6% | 31.03 ± 3.33** |
| Compound sea cucumber preparation 0.25 g/kg | 22.77 ± 2.19 | 5.2% | 27.42 ± 3.29 | 7.5% | 26.48 ± 3.55* | 11.9% | 25.00 ± 4.07** | 17.1% | 29.15 ± 2.17** |

Note:
compared with high plasma glucose model group
*$p < 0.05$,
**$p < 0.01$, compared with blank control group
Δ$p < 0.01$ D-2 Influences of Compound Sea Cucumber Preparation to Glucose Resistance of Experimental Diabetic Mice Caused by Alloxan

TABLE 4

Influences of compound sea cucumber preparation to glucose resistance of experimental diabetic mice caused by alloxan (n = 10, x ± s)

| Group | Fasting Plasma Glucose (FPG, mmol/L) | Plasma Glucose after glucose load (mmol/L) | | | | Area under the glucose load curve (ADC, mmol · h/L) | AUC reduce % |
|---|---|---|---|---|---|---|---|
| | | 30 min | 60 min | 120 min | 240 min | | |
| Blank control group | 7.35 ± 0.62 | 20.40 ± 2.42 | 19.22 ± 4.08 | 10.37 ± 2.31 | 6.86 ± 0.46 | 48.87 ± 7.00 | — |
| High plasma glucose group | 30.16 ± 2.40Δ | 33.30 ± 0.00 | 33.30 ± 0.00 | 33.30 ± 0.00 | 30.47 ± 2.31 | 129.59 ± 2.57Δ | — |
| metformin 200 mg/kg | 20.72 ± 3.03** | 31.68 ± 2.78 | 31.19 ± 3.42 | 27.43 ± 4.37 | 20.49 ± 2.58 | 106.05 ± 12.0** | 18.2% |
| Compound sea cucumber preparation 0.5 g/kg | 21.54 ± 3.43** | 33.30 ± 0.00 | 33.30 ± 0.00 | 30.59 ± 3.37 | 20.94 ± 3.68 | 113.84 ± 7.73** | 12.2% |
| Compound sea cucumber preparation 0.25 g/kg | 25.00 ± 4.07** | 33.30 ± 0.00 | 33.30 ± 0.00 | 33.25 ± 0.16 | 28.63 ± 1.98 | 126.38 ± 2.42 | 2.5% |

Note:
compared with high plasma glucose model group
*p<0.05,
**p<0.01, compared with blank control group
Δp < 0.01

D-3 Influences of Compound Sea Cucumber Preparation to Glucose Consumption and Glycerin Consumption of Insulin Resistance HepG2 Cells: See Table 5, 6:

TABLE 5

Influences of compound sea cucumber preparation to glucose consumption and glycerin consumption of insulin resistance HepG2 cells

| Group | Glucose consumption (mmol/L) | Glucose consumption increase % | Glycerin consumption (mmol/L) | Glycerin consumption increase % |
|---|---|---|---|---|
| Blank control group | 3.60 ± 0.27 | — | 0.51 ± 0.05 | — |
| Model group | 1.32 ± 0.13▲ | — | 0.15 ± 0.01▲ | — |
| metformin 30 mg/L | 2.83 ± 0.14** | 115.10% | 0.39 ± 0.02** | 165.97% |
| Compound sea cucumber preparation 2.5 g/L | 2.59 ± 0.15** | 96.60% | 0.38 ± 0.02** | 162.82% |
| Compound sea cucumber preparation 5.0 g/L | 2.82 ± 0.15** | 114.24% | 0.39 ± 0.02** | 167.02% |

Note:
compared with model group
*p < 0.05,
**p < 0.01;
compared with blank control group
▲p < 0.01

TABLE 6

Influences of compound sea cucumber preparation
to insulin resistance HepG2 cell proliferation

| Group | Cell survival % | Cell increase % |
|---|---|---|
| Blank control group | 100 ± 0 | — |
| Model group | 98.72 ± 1.37▲ | −1.28% |
| metformin 30 mg/L | 100.28 ± 1.93Δ | 0.28% |
| Compound sea cucumber preparation 2.5 g/L | 104.17 ± 6.78Δ | 4.17% |
| Compound sea cucumber preparation 5.0 g/L | 105.96 ± 5.80* | 5.96% |

Note:
compared with model group
*$p < 0.05$,
Δ$p > 0.05$,
compared with blank control group
▲$p > 0.05$ It can be known from Table 5 and Table 6 that, compound sea cucumber preparation can increase the glucose consumption of insulin resistance HepG2 cells by 96.6% and 114.2% respectively at the concentrations of 2.5 g/L and 5.0 g/L ($p<0.01$), increase the glycerin consumption respectively by 162% and 167% ($p<0.01$). At this concentration, the cell proliferation is only 4%-6%, so we can believe that the increases of above said glucose and glycerin consumptions are not caused by cell proliferation, but mainly caused by direct influences of glucose metabolism biochemical process by active ingredients of compound sea cucumber preparation.

The invention claimed is:

1. A compound sea cucumber product, comprising a sea cucumber extract and a panax pseudo-ginseng saponins extract,
    wherein the sea cucumber extract comprises a sea cucumber polysaccharide and a weight percentage of the sea cucumber polysaccharide is 2.5 wt % to 8.0 wt % of a total weight of the sea cucumber product,
    wherein a weight percentage of panax pseudo-ginseng saponins R1, Rb1 and Rg1 is 0.3 wt % to 21.0 wt % of the total weight of the sea cucumber product.

2. The compound sea cucumber product according to claim 1, wherein the product is in a form of capsules, tablets, or granules.

3. The compound sea cucumber product according to claim 1, wherein the sea cucumber extract is made from sea stichopus or cucumaria frondosa.

4. The compound sea cucumber product of claim 1, wherein said sea cucumber extract is obtained by a method comprising a step of enzymolysis, comprising:
    adding a sea cucumber powder in water to form a first mixture;
    adding proteinase to the first mixture to form a second mixture;
    adjusting the pH value of the second mixture to a predetermined value;
    heating the second mixture for a predetermined amount of time at a predetermined temperature;
    obtaining a supernatant from the second mixture; and
    drying the supernatant to obtain the sea cucumber extract.

5. The compound sea cucumber product according to claim 4, wherein a mass ratio of the sea cucumber powder to water in the first mixture ranges from 1:3 to 1:10.

6. The compound sea cucumber product according to claim 5, wherein a mass ratio of the sea cucumber powder to the proteinase in the second mixture ranges from 1 gram:0.1 mg to 1 gram:1010 mg.

7. The compound sea cucumber product according to claim 5, wherein the predetermined amount of time is 1 to 5 hours and the predetermined temperature is 40° C. to 70° C.

8. The compound sea cucumber product according to claim 5, wherein proteinase is chosen from bromelain, papain, alkali proteinase, neutral proteinase, flavourzyme, or trypsase.

9. The compound sea cucumber product according to claim 5, wherein the alkali proteinase is acalase.

10. The compound sea cucumber product according to claim 5, wherein the predetermined pH value ranges from 6-10.

11. The compound sea cucumber product according to claim 5, wherein the preparation method further comprising:
    a gelatination step wherein a sea cucumber is gelatinated in an airtight container at 70° C. to 130° C. for 1 min to 20 hours;
    a freeze-dry step wherein the gelatinated sea cucumber is freeze-dried till the water content is less than 10 wt %;
    one or more crush steps wherein the freeze-dried sea cucumber is crushed into the sea cucumber powder; and
    a mixing step wherein the sea cucumber extract is mixed with the panax pseudo-ginseng saponins extract at the ratio ranging from (99% to 70 wt %):(1 wt % to 30 wt %).

12. The compound sea cucumber product according to claim 11, wherein the sea cucumber powder has a particle size in the range of 10 nm to 1000 nm.

13. The compound sea cucumber product according to claim 1, wherein a weight percentage of the sea cucumber extract is 70 wt % to 99 wt % and a weight percentage of the panax pseudo-ginseng saponins extract is 1 wt % to 30 wt %.

14. The compound sea cucumber product according to claim 1, the product is an anticoagulant or an anti-diabetic medication.

15. A method for manufacturing the compound sea cucumber preparation product according to claim 1, comprising the following steps:
    (1) Raw material processing: put the cut and leaned fresh sea cucumber or soaked sea cucumber into an airtight container;
    (2) Heat and gelatination: at 70 to 130° C., gelatinate for 1 min to 20 hours;
    (3) Freeze-dry: freeze-dry the gelatinated sea cucumber till the water content is less than 10 wt %;
    (4) Coarse crush: crush the freeze-dried sea cucumber for 1 to 20 min to obtain sea cucumber powder with fineness of 10 to 300 mesh;
    (5) Ultra-micro crush: ultra-micro crush the coarse crushed sea cucumber powder with an airflow crusher, to obtain the ultra-micro sea cucumber powder with fineness of 100 to 3000 mesh;
    (6) Nanometer crush: nanometer crush, by means of a high energy ball grinding mill, the ultra-micro sea cucumber powder obtained by the airflow crusher, the crushing time being 4 to 20 hours, to obtain a fineness of up to 10 to 1000 nm;
    (7) Enzymolysis and separation: dissolve the nanometer sea cucumber powder with water at the mass ratio of 1:3 to 10, add proteinase at the ratio of nanometer sea cucumber powder:proteinase equal to 1 g:0.1 to 1010 mg and enzymolysis at corresponding pH value for 1 to 5 hours at 40 to 70° C., then apply heat to inactivate the proteinase, centrifuge at 0 to 10° C., take the supernatant and carry out drying to obtain nanometer sea cucumber extract;

(8) Mix the nanometer sea cucumber extract with the panax pseudo-ginseng saponins extract at the ratio of nanometer sea cucumber extract:panax pseudo-ginseng saponins extract equal to 99 to 70 wt %:1 to 30 wt %.

16. The method according to claim 15 for manufacturing said compound sea cucumber, wherein at step (1) the varieties of said fresh sea cucumber or soaked sea cucumber used are sea stichopus or cucumaria frondosa; said soaked sea cucumber is made by soaking or desalinating dry sea cucumber, half-dried sea cucumber or saline sea cucumber.

17. The method according to claim 15 for manufacturing said compound sea cucumber, wherein the heating and gelatination at step (2) are carried out at 100 to 105° C. for 1 hour.

18. The method according to claim 15 for manufacturing said compound sea cucumber, wherein the freeze-drying at step (3) is carried out till the water content is less than 3%.

19. The method according to claim 15 for manufacturing said compound sea cucumber, wherein the proteinases for enzymolysis and enzymolysis during separation at step (7) are any 1 to 3 types selected from bromelain, papain, alkali proteinase, neutral proteinase, flavourzyme, trypsase.

20. The method according to claim 15 for manufacturing said compound sea cucumber, wherein the enzymolysis and separation at step (7) comprises: evenly mix the nanometer sea cucumber powder with water at the mass ratio of 1:7, use alkali proteinase acalase and trypsase to carry out double enzymolysis: the temperature for enzymolysis is 40 to 70° C., firstly adjust the pH value to 7 to 8, add alkali proteinase acalase according to the mass ratio between nanometer sea cucumber powder and proteinase equal to 1 g:0.1 to 10 mg, after enzymolysis for 0.1 h to 5 h, adjust pH value to 8 to 10, add trypsase according to the mass ratio between nanometer sea cucumber powder and proteinase equal to 1 g:10 mg to 1000 mg to enzymolysis for 0.1 to 5 h for the second time at 40 to 70° C., inactivate the proteinase after the enzymolysis reaction is finished, then filter, centrifuge and separate the enzymolysis product, take the enzymolysis supernatant and dry to get nanometer sea cucumber extract.

* * * * *